United States Patent [19]

Adams et al.

[11] Patent Number: 4,740,621

[45] Date of Patent: Apr. 26, 1988

[54] CO-PRODUCTION OF AN AROMATIC MONOAMINE AND AN AROMATIC DIAMINE DIRECTLY FROM BENZENE OR A BENZENE DERIVATIVE THROUGH CONTROLLED NITRATION

[75] Inventors: Earl G. Adams, Grand Bay, Ala.; Robert B. Barker, Gautier, Miss.; Mark J. Lossett, Gautier, Miss.; Larry I. Flowers, Gautier, Miss.

[73] Assignee: First Chemical Corporation, Pascagoula, Miss.

[21] Appl. No.: 793,788

[22] Filed: Nov. 1, 1985

[51] Int. Cl.⁴ .............................................. C07C 85/11
[52] U.S. Cl. .................................................... 564/419
[58] Field of Search ........................................ 564/419

[56] References Cited

U.S. PATENT DOCUMENTS

| | | | |
|---|---|---|---|
| 2,454,468 | 11/1948 | McArdle | 564/419 |
| 4,287,365 | 9/1981 | Becker et al. | 564/419 X |
| 4,340,758 | 7/1982 | Lapporte et al. | 564/419 X |
| 4,433,169 | 2/1984 | Scholl | 564/419 |

Primary Examiner—Paul F. Shaver
Attorney, Agent, or Firm—A. W. Breiner

[57] ABSTRACT

A two-stage process for the co-production of aniline and m-phenylenediamine where, in the first stage, benzene, nitric acid, and sulfuric acid are reacted in a liquid phase to produce in greater amounts nitrobenzene (approximately 70%) and m-dinitrobenzene (approximately 30%), and in lesser or trace amounts o-dinitrobenzene and p-dinitrobenzene, and water; and in the second stage the products of the first stage are reacted with hydrogen in the gas phase to produce aniline (approximately 70%) and m-phenylenediamine (approximately 30%) in greater amounts, and o-phenylenediamine and p-phenylenediamine in lesser amounts, and water. The reaction products are separated by distillation. The first stage of a preferred embodiment of the process is characterized in that a concentrated mixture of nitric acid and sulfuric acid are fed along with mononitrobenzene to a first reactor for producing dinitrobenzene, and then the dilute acid mixture recovered from this first reactor is fed along with benzene to a second reactor for producing the mononitrobenzene used as a reactant in the first reactor. The second stage, which provides the aniline and m-phenylenediamine in major amounts, is characterized in that the hydrogenation is carried out in the gas phase with product aniline serving as a diluent. The process is applicable to the co-production of other aromatic mono- and diamines.

33 Claims, 1 Drawing Sheet

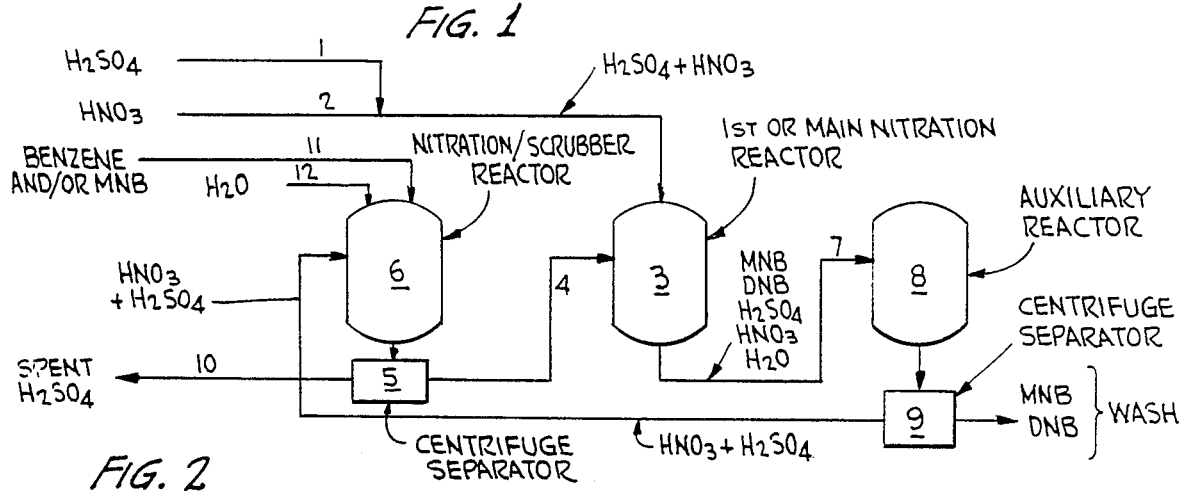
FIG. 1
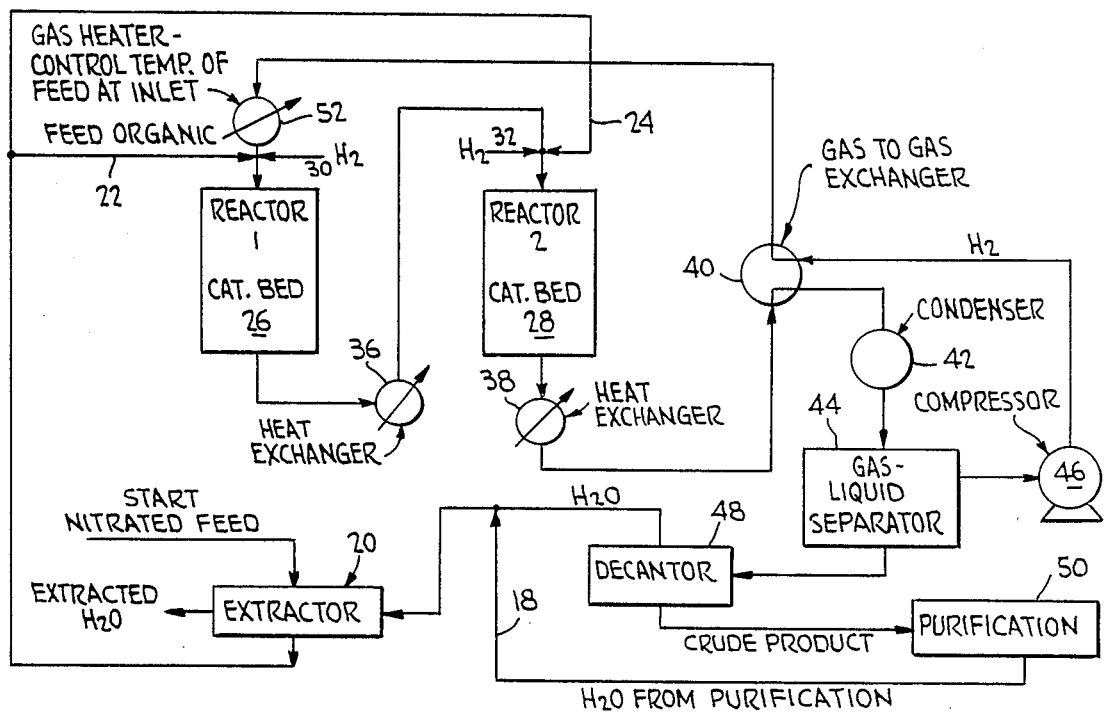
FIG. 2
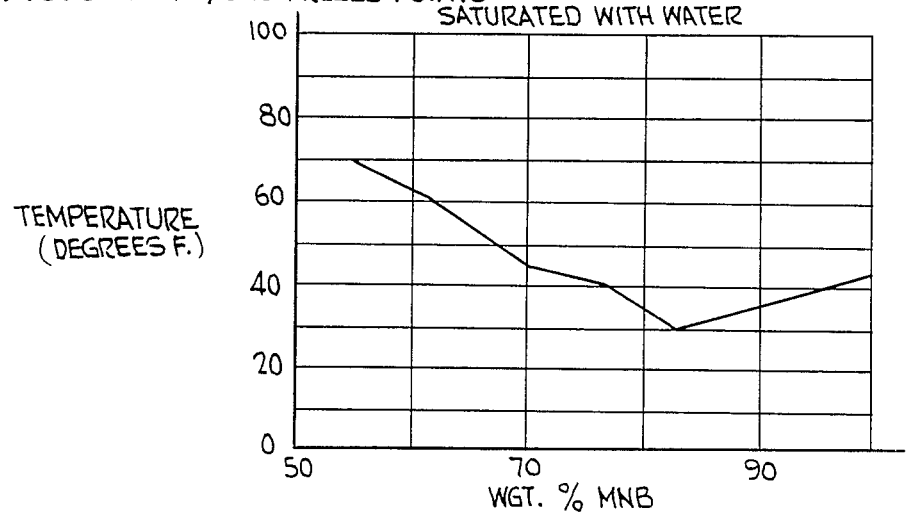
FIG. 3 MNB/DNB FREEZE POINTS - SATURATED WITH WATER

CO-PRODUCTION OF AN AROMATIC MONOAMINE AND AN AROMATIC DIAMINE DIRECTLY FROM BENZENE OR A BENZENE DERIVATIVE THROUGH CONTROLLED NITRATION

FIELD OF INVENTION

This invention relates primarily to the co-production of an aromatic monoamine and an aromatic diamine directly from benzene or a benzene derivative through controlled nitration. More particularly, this invention relates to a two-stage process for the efficient co-production of aniline and m-phenylenediamine by the direct nitration of benzene and subsequent reduction.

BACKGROUND OF INVENTION m-Phenylenediamine has been commonly produced by the reduction of m-dinitrobenzene. This process is relatively expensive in that the m-dinitrobenzene utilized is obtained through the complete dinitration of benzene which is then separated and purified prior to the reduction. This purification involves reaction with a substance such as sodium sulfite which places the undesirable o-dinitrobenzene and p-dinitrobenzene into an aqueous phase resulting in a large amount of waste water as disclosed, for example, in U.S. Pat. No. 3,086,063. The m-phenylenediamine must then be separated from reaction impurities after the reduction. m-Phenylenediamine has also been produced by reduction of dinitrobenzene, followed by separation of m-phenylenediamine from o-phenylenediamine and p-phenylenediamine. Although less expensive than the above method, the dinitrobenzene utilized is obtained through complete dinitration of benzene which must be extracted or separated as a solid from the reaction medium.

More recently, U.S. Pat. No. 4,185,036 disclosed the hydrogenation of a mixture of an aromatic mononitro compound and an aromatic dinitro compound in the liquid phase. According to the process, hydrogen and a homogeneous or heterogeneous liquid mixture of at least 25 wt. % of an aromatic dinitro compound and/or at least 25 wt. % of a mononitro monoamino compound and at least 25 wt. % of an aromatic mononitro non-amino compound are reacted with vigorous mixing in the presence of a hydrogenation catalyst at a temperature of from about 75° to 225° C. and a pressure of about 50 to 800 psi. According to the patent, pure or relatively pure nitro products are used in the process as the starting materials to produce a mixture of the monoamino and diamino compounds which are then separated by distillation. Accordingly, the process is relatively expensive because of the need to separate and purify the starting materials and then the final products; and, additionally, the reaction rates in the liquid-phase hydrogenation are relatively slow, resulting in high energy consumption and low reactor utility.

OBJECTS AND GENERAL DESCRIPTION OF INVENTION

It is a primary object of the present invention to provide a process for the co-production of aniline and m-phenylenediamine which is relatively rapid and inexpensive.

It is another object of the invention to provide a two-stage process for the co-production of aniline and m-phenylenediamine directly from benzene and nitric acid without need for isolation and isomer purification of dinitrobenzene.

It is another object of the present invention to provide a method of producing m-phenylenediamine from benzene in a totally continuous process.

It is another object of the present invention to provide a process for the co-production of an aromatic monoamine and an aromatic diamine directly from benzene or a benzene derivative and nitric acid without need for intermediate isomer purification or separation.

The above and other objects of the invention will be apparent from the following general description and the detailed presently preferred embodiments.

In accordance with the present invention, in a first stage benzene is reacted with nitric acid in the presence of sulfuric acid in the liquid phase to produce mononitrobenzene and m-dinitrobenzene in greater amounts, and o-dinitrobenzene and p-dinitrobenzene in lesser or trace amounts. This first stage is characterized in that in a preferred embodiment the benzene is nitrated in two reactors. In the one reactor benzene is converted to mononitrobenzene, and in a second reactor about 40 to 20% of the mononitrobenzene is converted to dinitrobenzene. The percentage converted to the dinitrobenzene is critical only to the extent that it should be below the amount where crystallization of the dinitrobenzene will occur. At this stage of the nitration the dinitrobenzene is soluble in the mononitrobenzene which is at a point near a eutectic in the freezing point curve of the mononitro and dinitrobenzene. This is especially beneficial since the nitration can be carried out in one step without extra extraction or without an added solvent. It is noted, however, that at even this relatively low level of nitration the formation of the dinitrobenzene is a slower reaction requiring more strenuous conditions than is the formation of the mononitrobenzene. Accordingly, in a disclosed preferred embodiment of the process a strong or concentrated mixture of nitric and sulfuric acid is fed to the dinitration reactor for the formation of the dinitrobenzene from mononitrobenzene. The dilute acid by-product of the dinitration reaction containing a mixture of nitric and sulfuric acids and a small amount of dinitrobenzene is fed to the mononitration reactor where it is mixed with additional sulfuric and nitric acid, and reacted with benzene to form the mononitrobenzene. There is, therefore, a counterflow of mononitrobenzene and dinitration by-product acid between the two reactors. This counterflow is advantageous in that, since mononitration needs a less concentrated acid, the same sulfuric acid is used in each reactor; and, also, dinitrobenzene dissolved in the dinitration by-product acid is extracted with benzene and mononitrobenzene and recycled through the system. In an alternative embodiment, mononitrobenzene is the starting material and is nitrated to a 40-20% solution of dinitrobenzene. This alternative method does not have the benefits outlined for the counterflow method. As another modification of these embodiments, auxiliary reactors can be used downstream of the main reactor to improve efficiency of the dinitration and mononitration reactions. The reaction mixture of monoand dinitrobenzenes, without dinitrobenzene separation or isomer purification, is subjected in a second stage to hydrogenation in the gas phase in the presence of a catalyst. The products of the reaction are aniline in the major amount, m-phenylenediamine in a lower amount, and the o-phenylenediamine and p-phenylenediamine in trace amounts. This stage of the process is characterized in that the reaction is carried out in the gas phase and in that the liquid product of the reaction, i.e., aniline, serves as a product diluent. The products of the reaction are separated by distillation. The reaction proceeds as follows:

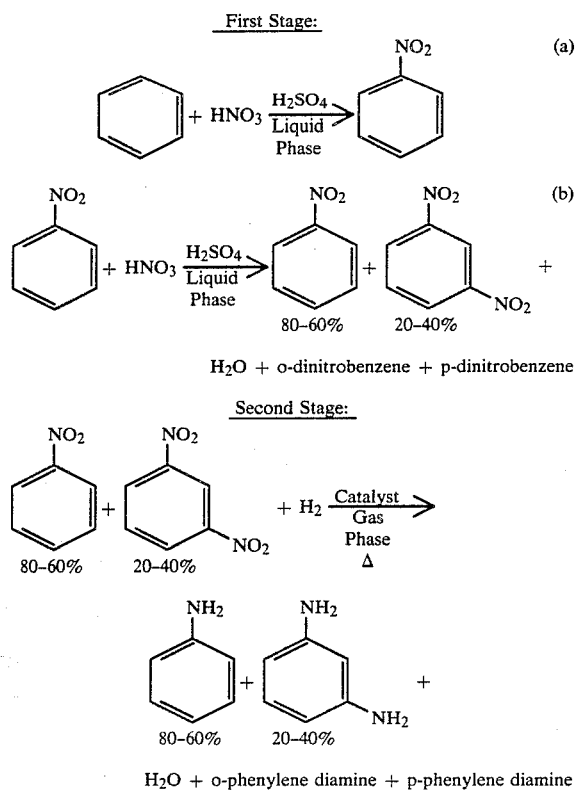

A primary advantage of the process of this invention is in the ability to proceed directly from benzene to the final aromatic mono- and diamino products without need for separation or isomer purification of the intermediate materials, i.e., the mononitrobenzene and dinitrobenzene. A further advantage is that because of the ability to carry out the first stage of the reaction in the liquid phase and the second stage of the reaction in the gas phase using aniline as a product diluent, it is possible to prepare the high melting point m-phenylenediamine in existing relatively low-cost processing equipment. This eliminates the need for specialized equipment to prepare the high melting point materials. Accordingly, it is possible to produce what heretofore have been "specialty chemicals" or chemicals requiring special processing as a coproduct of commercial aniline production. This two-stage process, with the first stage occurring in the liquid phase and the second stage occurring in the gas phase with aniline as diluent, provides substantial commercial advantages. A further important advantage is that in using the countercurrent flow of reactants in the first stage of the process, i.e., the mononitrobenzene and mixture of dilute nitric and dilute sulfuric acid, between the two reactors greater efficiencies and shorter processing times are possible, reducing the energy consumption of the process.

While the invention is being described primarily with reference to the co-production of aniline and m-phenylenediamine, it will be apparent to those skilled in the art that the process can be utilized to produce analogous monoamino and diamino compounds directly from a derivative of benzene, with the intermediate nitro and dinitro products being formed. As will also be recognized by one skilled in the art, the processing conditions can be varied to provide more highly nitrated compounds by increasing the amount of nitric acid and sulfuric acid utilized in the first stage of the reaction.

PRESENTLY PREFERRED EMBODIMENTS

Having described the invention in general terms, presently preferred embodiments will be set forth in reference to the drawing wherein FIG. 1 is a reactor scheme for the production of mononitro and dinitrobenzene from benzene or dinitrobenzene from mononitrobenzene according to the first stage of the process of the present invention;

FIG. 2 is a reactor scheme for the gas phase hydrogeneration of nitrobenzenes according to the second stage of the process of the present invention; and FIG. 3 is a freezing point curve of mixtures of mononitro and dinitrobenzene saturated with water.

In the preferred embodiments, parts are by weight unless otherwise specified.

Referring first to FIG. 1 of the drawing, the reactor system utilized in the first stage of the process of this invention comprises a plurality of reactors 3, 6, and 8 for carrying out a continuous, liquid-phase nitration process. This reactor system includes the reactors needed for the production of dinitrobenzene directly from benzene. However, the system can also be operated as described hereinafter in Example 1 utilizing mononitrobenzene as the primary feed to produce dinitrobenzene. Further, two such systems can be used in combination, as described hereinafter in Example 2, to produce mononitrobenzene and dinitrobenzene directly from benzene. The entire system is constructed of stainless steel. Further, each reactor of the system contains an agitator, not shown, and the liquid within the reactors is well agitated throughout this stage of the process. Temperature control is maintained by internal heat-exchangers in each reactor, again not shown, as is conventional.

Referring now to FIG. 2 of the drawing, the hydrogenation system utilized in the second stage of the process utilizes a pair of gas-phase reactors 26 and 28 arranged in series, each including a catalyst bed. The system, as will be more fully described in the working examples, includes in addition to the reactors, a gas heater 52 for heating the reactants, heat-exchangers 36, 38, gas-to-gas exchanger 40, condensor 42, compressor 46, gas-liquid separator 44, extractor 20, and purifier 50. The hydrogen gas is used to partially control the temperature of the system.

EXAMPLE 1

In a method of producing m-phenylenediamine from mononitrobenzene, referring to FIG. 1 of the drawing, sulfuric acid and nitric acid from inlets 1 and 2 are premixed and fed continuously into the first or main nitration reactor 3. An organic stream 4 containing mostly nitrobenzene with minor quantities of benzene and dinitrobenzene is fed continuously from scrubber/nitration reactor 6 into the main nitration reactor 3 passing through separator centrifuge 5 where spent $H_2SO_4$ with trace amounts of $HNO_3$ are separated for regeneration. Most of the nitration of the mononitrobenzene occurs in the main nitration reactor 3. However, in the embodiment shown, an auxiliary reactor 8 is utilized for greater efficiency. Thus, a mixture containing mostly nitrobenzene, dinitrobenzene, $H_2SO_4$, and $H_2O$ with a small amount of $HNO_3$ flows continuously from reactor 3 through inlet 7 into the auxiliary nitration reactor 8 where the reaction is allowed to go to completion. The mixture of reaction product from reactor 8 is removed continuously and passed through centrifuge separator 9 where the dilute acid and nitrated products are separated. The nitrated products from centrifuge 9 consisting mostly of nitrobenzene and dinitrobenzene with some dissolved acid and by-products are washed with NaOH and $H_2O$ to remove the trace acids and oxidation by-products. The dilute acid from centrifuge 9 is sent continuously to the scrubber/nitration reactor 6 where it is reacted with a continuous fresh stream of mononitrobenzene, with a small amount of benzene added through inlet 11. Water is added through inlet 12 as needed to decrease the dilute acid concentration to approximately 70% $H_2SO_4$. The mixture from the scrubber/nitration reactor 6 is continuously removed passing through centrifuge separator 5 where the organics are separated from spent acid. The organic stream 4 flowing from separator 5 consisting mostly of mononitrobenzene containing a small amount of dinitrobenzene is sent to the main reactor 3 as stated above. The spent acid stream 10 from centrifuge separator 5 consisting mostly of 70% $H_2SO_4$ may be regenerated or used for other purposes.

In the embodiment shown, the nitration reaction is controlled to obtain about 70% mononitrobenzene and about 30% dinitrobenzene. However, it is possible and it may be desirable to control the ratio of mononitrobenzene and dinitrobenzene in the range of from about 60% to 80% mononitrobenzene and 40% to 20% dinitrobenzene. Within this ratio the reaction readily proceeds and it is not necessary to utilize special equipment or solvent means to avoid crystallization of the nitrobenzene or to compensate for other characteristics of the dinitrobenzene. As illustrated in FIG. 3, a mixture of mononitrobenzene and dinitrobenzene within this range, saturated with water, is near a eutectic point in the freeze point curve. This permits nitration in one step without utilizing extra extraction or without an added solvent. Further, the same solution of the nitrobenzene and dinitrobenzene reaction can be hydrogenated in the described system. The amount of conversion of nitrobenzene to dinitrobenzene can be controlled within the desired range by adjusting the sulfuric acid and nitric acid feed or by adjusting the nitrobenzene feed to reactor 3.

The system illustrated in FIG. 1 was started up by filling vessel 6 and vessel 3 with mononitrobenzene and 70% $H_2SO_4$ containing some $HNO_3$. A feed of mononitrobenzene with benzene was fed to the scrubber/nitration reactor 6, and a pre-calculated amount of $H_2SO_4$ (98%) and nitric acid (63%) was fed to the main nitrator 3. The rates of feed of the mononitrobenzene, $H_2SO_4$, and $HNO_3$ were adjusted to get the desired product composition. Throughout this process the composition of the spent acid from the scrubber/nitration reactor 6 was adjusted to 70% by addition of water. This adjustment is necessary in order to maintain a low level of dinitrobenzene in the spent acid. The system was sampled every hour for organic and acid composition and feed rates were adjusted for the desired results. The temperature of the reactors were controlled for the desired results throughout the reaction. The feed rates, temperature, and compositions were then recorded as the optimum conditions for the reactor system. The optimum feed rate was 3.2 parts mononitrobenzene, 3.18 parts $H_2SO_4$ (98%), and 1.0 parts $HNO_3$ (63%).

The organic product of the reaction at reactors 3 and 8 consisted of mononitrobenzene (65%) and dinitrobenzene (35%). A small amount of acid was contained in the organic product. The dilute acid after passing through separator 9 had the composition of $H_2SO_4$, 77.7%; $HNO_3$, 0.8%; $H_2O$, 16.3%; nitrobenzene, 2.4%; and dinitrobenzene, 2.8%. The spent acid from the scrubber/nitration reactor 6 contained 72.5% $H_2SO_4$, 0.04% $HNO_3$, and traces of mononitrobenzene and dinitrobenzene. The organic feed from the scrubber/nitration reactor 6 to the main nitration vessel 3 consisted of nitrobenzene, 91.9%; dinitrobenzene, 4.6%, and benzene, 3.5%. The temperatures of the reactors at the optimum conditions were controlled at 42° C. for the scrubber/nitration reactor 6, 53° C. for the main nitration reactor 3, and 55° C. for the auxiliary nitration vessel 7. The amount of nitrobenzene to dinitrobenzene was easily controlled within the desired range of 60% to 80% mononitrobenzene and 40% to 20% dinitrobenzene by adjusting the sulfuric and nitric feed; or by adjusting the mononitrobenzene feed to reactor 3. No crystallization of dinitrobenzene was observed during this process. The by-product acid contained only traces of organic residue. The mononitrobenzene/dinitrobenzene product was ready for reduction after NaOH/water wash.

Referring now to FIG. 2 for the second stage of the process according to this invention, a catalyst bed containing equal volumes of copper containing hydrogenation catalyst were provided in each of reactors 26 and 28. These beds were connected in series with provisions for temperature regulation at the inlet and outlet of each bed. Provisions were made to circulate hydrogen through the beds and heat-exchangers at about 8 psig and at a flow rate of 25 bed volumes per minute. This circulating hydrogen stream provided hydrogen for the reduction process and also acted as a heatsink for the heat of reaction. Hydrogen flow carried heat away from the reactors as fast as it was formed. This heated hydrogen stream passed through heat-exchangers 36, 38 and produced steam for product purification. The organic feed was atomized into the circulating gas stream with fresh hydrogen. Good atomization was found to prevent carbon deposition at the reactor inlet. The atomizing hydrogen also replaced hydrogen consumed in the reaction.

A typical feed composition to the hydrogenation reactor was as follows:
  Aniline: 6.7% w/w
  Phenylenediamine (all isomers): 3.0% w/w
  Dinitrobenzene (all isomers): 30% w/w
  Benzene: 0.1% w/w
  Mononitrobenzene: Balance of feed stream
The aniline and diamine were from the extraction process at extractor 20 of the system which extracted nitrogen compounds from the water of reaction from decanter 48 and also from water 18 from the purification step 50 of the process. This extraction removes practically all amine compounds from the water stream.

The reactor feed coming from extractor 20, as further illustrated in FIG. 2, was split into nearly equal streams 22 and 24 for feeding to the two reactor beds 26 and 28. Slightly more reactor feed could be used by the second reactor and still maintain the desired temperature maximum of about 600° F. The higher total weight of materials passing through the second bed allows for more heat removal from the system and allows more feed to be used. Typical reactor feed rates were 2.25 pounds/day/pound of catalyst the first reactor, and 2.5 pounds/day/pound of catalyst for the second reactor. The temperatures at these feed rates were as follows: inlet to reactor 26°–359° F.; outlet of reactor 26°–531° F., with hot spots of 600° F.; inlet to reactor 28°–399° F.; outlet of reactor 28°–566° F., with the highest bed temperature being 572° F. Hydrogen was fed continuously to each of reactors 26 and 28 through inlets 30 and 32, respectively, along with the feeding of the organics or nitrated benzenes to be hydrogenated. In the embodiment shown, the organic reactants which are fed to the reactors are heated by the hydrogen from gas heater 52.

As also shown in FIG. 2, reactors 26 and 28 which are connected in series have a heat-exchanger 36 between the two reactors for controlling the temperature of the output of reactor 26. A second heat-exchanger 38 is at the outlet of reactor 28 to again control the temperature of the hydrogenation product. The hydrogenation product is fed from heat-exchanger 38 through a gas-to-gas exchanger 40 to a condenser 42 and into a gas-liquid separator 44. The hydrogen removed by the gas-liquid separator 44 is passed through compressor 46 through the gas-to-gas exchanger 40, and through gas heater 52 for utilization at the reactors. In this way the hydrogen functions as a temperature control means or a heatsink. The liquid from separator 44 passes through decanter 48, with the crude product then directed to purification unit 50 for final purification. Water from decanter 48 and purification unit 50, as above stated, flows to extractor 20.

The reactor product was analyzed and the organic layer was found to contain the following:

Aniline: 72.7%
Phenylenediamine (all isomers): 26.6%
Heavy Compounds: 0.1%
Benzene and Light Compounds: 0.7%

The benzene content was due to the trace levels of benzene in the feed being removed from the product during the purification step and then being returned to the reaction system through the extraction step. No nitro compound was found in the reactor product, and no sign of abnormal catalyst deactivation was noted. During this production run, about 62,000 pounds of diamine was produced. After this production run, the catalyst was regenerated by oxidation with air, reduced with hydrogen, and appeared to have full activity. The m-phenylenediamine was easily separated using conventional purification procedures.

EXAMPLE 2

This embodiment was carried out utilizing two reaction apparatus designed similar to the system shown in FIG. 1. The embodiment was run so as to produce dinitrobenzene (30–35%) from mononitrobenzene in Reactor System I and mononitrobenzene from benzene in Reactor System II. The by-product acid from reactor System I was used as feed acid for the mononitration (System II), and the mononitrobenzene produced in System II was used as feed for the dinitration (System I). Hence, the counterflow method, as described earlier, was obtained. System II was started up and brought to equilibrium as described in Example 1. The main reactor of System I was charged continuously with 4.03 parts mononitrobenzene, 3.18 parts H₂SO₄ (98%), and 1.0 parts HNO₃ (63%). The system was well agitated at 58° C. The organic product was composed of mononitrobenzene (65%) and dinitrobenzene (35%), with trace amounts of acids and oxidation by-products. The by-product acid from this System I was fed continuously into System II with 1.05 parts benzene, and extra acid of the composition 1.35 parts HNO₃ (63%) and 1.0 parts H₂SO₄ (98%). The system was well agitated at 55° C. The product of this reaction was composed of mostly mononitrobenzene with trace amounts of benzene and acid. This product can now be used as fed for dinitration in System I.

EXAMPLE 3

In an analogous process to the process of Example 2, benzene was replaced with toluene. The toluene was first nitrated, and the nitration products hydrogenated as in Example 2 to produce mixed toluidine isomers and mixed toluene diamine isomers. The composition of the reaction is controlled to provide the desired ratios of products.

EXAMPLE 4

In the process of Example 1, the mononitrobenzene was replaced with o-nitrotoluene and nitrated as in Example 1. The nitrated product consisting mostly of o-nitrotoluene, 2,4-dinitrotoluene and 2,6-dinitrotoluene was then hydrogenated, as described in Example 1, to produce o-toluidine, 2,4-toluenediamine, and 2,6-toluenediamine. The composition of the reaction is controlled to provide the desired ratios of products.

In Example 1 of this application mononitrobenzene was primarily fed to scrubber/nitration reactor 6 in place of benzene. In Example 2 to describe the countercurrent flow technique of the preferred embodiment of this invention, two separate reactor systems essentially as shown in FIG. 1 were utilized in combination. The system of FIG. 1, however, can be used as illustrated in a continuous process to produce mononitrobenzene and dinitrobenzene in controlled amounts directly from benzene. The system was utilized as in Examples 1 and 2 in order to more conveniently illustrate the characteristics of the disclosed invention. Also in accordance with the present process, as shown in Examples 3 and 4, a benzene derivative can be substituted for benzene to co-produce mono and diamines. In the process, the benzene or benzene derivative will have the structure

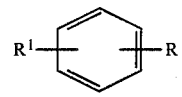

wherein R and R¹ are each hydrogen or alkyl having from 1 to 5 carbon atoms.

The presently disclosed process permits operation within advantageous temperature ranges. Specifically, the nitration reactions can advantageously be carried out at from about 30° to 85° C., and preferably where a plurality of reactors are employed the scrubber/nitration reactor will be at a temperature of from about 35° to 55° C.; the main nitration reactor at from about 40° to 70° C., and, if utilized, the auxiliary nitration reactor will be at a temperature of from about 45° to 70° C. The hydrogenation reaction, being carried out in the gas phase, provides high yields utilizing non-noble metal catalysts, such as copper, which again lowers the cost of the process. Since the reaction is heterogeneous gas phased, the catalyst bed remains in place, eliminating the need for filtration as in a batch liquid-phase process. The catalyst used in the gas-phase reaction is a heterogeneous catalyst as opposed to a homogeneous catalyst, which also provides a cost advantage. Since the reaction at high temperatures proceeds without pressurization, the capital costs of the plant are lower.

An additional important advantage of the counterflow process herein described is in the nature of the by-products. The dinitration of benzene will produce a spent acid which contains large amounts of dinitrobenzene, phenolic compounds, and other oxidized by-products. When starting with benzene and utilizing the countercurrent flow method, as described as a preferred embodiment of this invention, a spent acid is produced which is substantially equivalent to the spent acid obtained in a mononitration process. This spent acid is "clean" and substantially easier to work with in a recovery process—for example, by re-concentration; or for direct use—for example, in a phosphoric acid plant.

A primary advantage of the hydrogenation reaction of the present invention is that the feedstock for the reaction is a liquid. This permits the direct utilization of the liquid reaction product of the nitration stage of the process. The reduction of the mononitro compounds produces less heat per mole and moderates the reaction temperature. Further, a synergistic effect in the co-reduction of the mono- and dinitrobenzenes is that less carbon is formed in the dinitro reduction when a mononitro compound is co-reduced with the dinitro compound. This synergistic effect, whereby less carbon is formed, leads to a greater catalyst life which extends run time and lowers production costs. Further, the large amount of monoamine in the reactor product extracts most of the water-soluble diamines from the water of reaction, which simplifies the purification of the final product. Just as the monoamine causes the diamine to be extracted from the reaction water, it also prevents the water from being highly soluble in the organic phase and precludes the need to distill out large amounts of water in the purification process. This feature leads to substantial energy savings and allows smaller distillation equipment for a given amount of product. The aforesaid and other advantages of the co-production process of the present invention are apparent from the above disclosure.

As will be apparent to one skilled in the art, various modifications can be made within the scope of the aforesaid description. Such modifications being within the ability of one skilled in the art form a part of the present invention and are embraced by the appended claims.

It is claimed:

1. A continuous two-stage process for the co-production of aniline and m-phenylenediamine by the direct nitration of benzene comprising the steps of
   (A) in a first stage reacting benzene with a mixture of nitric acid and sulfuric acid, said reaction being controlled to provide a mixture of from about 60% to about 80% mononitrobenzene and 40% to 20% dinitrobenzene;
   (B) in a second stage subjecting said mixture of mononitrobenzene and dinitrobenzene of step (A) to a gas phase hydrogenation reaction comprising contacting said mixture in the gas phase with hydrogen in the presence of a catalyst to provide a mixture containing about 60% to about 80% aniline and about 40% to about 20% m-phenylenediamine; and
   (C) separating said aniline and m-phenylenediamine from said mixture.

2. The process of claim 1 wherein in said first stage benzene is reacted with said nitric and sulfuric acid in two steps, wherein in the first of said two steps a mixture of concentrated sulfuric and nitric acid is reacted with mononitrobenzene to provide a mixture of about 60% to about 80% mononitrobenzene and about 40% to about 20% dinitrobenzene and dilute sulfuric and nitric acids; separating said mononitrobenzene and dinitrobenzene from said acid mixture and then reacting in the second of said two steps said dilute nitric and sulfuric acid with benzene to provide mononitrobenzene, and using said mononitrobenzene in said first of said two steps.

3. The process of claim 1 wherein said nitration of benzene is controlled whereby said mixture of mononitrobenzene and dinitrobenzene is present at about 70% mononitrobenzene and about 30% dinitrobenzene.

4. The process of claims 2 or 3 wherein said mixture of mononitrobenzene and dinitrobenzene is separated from said dilute acid mixture by centrifugation or decantation.

5. The process of claim 1 wherein in step (B) said hydrogenation is carried out by passing said mixture of mononitrobenzene and dinitrobenzene when in the gaseous form in the presence of hydrogen gas through a catalyst bed.

6. The process of claim 5 wherein said catalyst bed is divided into two parts connected in series with about 50% of the mononitrobenzene and dinitrobenzene being fed to each of said two parts of catalyst bed.

7. The process of claim 6 wherein aniline is utilized as a diluent in said hydrogenation product.

8. The process of claim 2 wherein the temperature in the first of said two steps is at from about 40° to 70° C.

9. The process of claim 2 wherein the temperature in the second of said two steps is at from about 35° to 55° C.

10. The process of claim 8 wherein said first of said two steps is carried out in two stages in a main reactor and an auxiliary reactor, and the temperature in the main reactor is at from about 40° to 65° C. and the temperature in the auxiliary reactor is at from about 45° to 70° C.

11. The process of claim 1 wherein the temperature of the hydrogenation reaction is at from about 350° to about 650° F.

12. A continuous two-stage process for the co-production of an aromatic monoamine and an aromatic diamine by the direct nitration of benzene or a benzene derivative comprising the steps of
   (A) in a first stage reacting a benzene compound having the formula

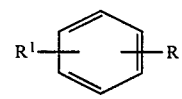

wherein R and R¹ are each hydrogen or alkyl of from 1 to 5 carbon atoms, with a mixture of nitric acid and sulfuric acid, said reaction being controlled to provide a mixture of from about 60% to about 80% of the mononitro compound and 40% to 20% dinitro compound;
   (B) in a second stage subjecting said mixture of mononitro and dinitro compounds of step (A) to a gas phase hydrogenation reaction comprising contacting said mixture in the gas phase with hydrogen in the presence of a catalyst to provide a mixture containing about 60% to about 80% of the aromatic monoamine and about 40% to about 20% of the aromatic diamine; and
   (C) separating said aromatic monoamine and aromatic diamine from said mixture.

13. The process of claim 12 wherein in said first stage said benzene compound is reacted with said nitric and sulfuric acid in two steps, wherein in the first of said two steps a mixture of concentrated sulfuric and nitric acid is reacted with the mononitrobenzene compound to provide a mixture of about 60% to about 80% mononitrobenzene compound and about 40% to about 20% dinitrobenzene compound and dilute sulfuric and nitric acids; separating said mononitrobenzene compound and dinitrobenzene compound from said acid mixture and then reacting in the second of said two steps said dilute nitric and sulfuric acid with said benzene compound to provide the mononitrobenzene compound, and using said mononitrobenzene compound in said first of said two steps.

14. The process of claim 12 wherein said nitration of said benzene compound is controlled whereby said mixture of mononitrobenzene compound and dinitrobenzene compound is present at about 70% mononitrobenzene compound and about 30% dinitrobenzene compound.

15. The process of claims 13 or 14 wherein said mixture of said mononitrobenzene compound and dinitrobenzene compound is separated from said dilute acid mixture by centrifugation.

16. The process of claim 12 wherein in step (B) said hydrogenation is carried out by passing said mixture of mononitrobenzene compound and dinitrobenzene compound when in the gaseous form in the presence of hydrogen gas through a catalyst bed.

17. The process of claim 16 wherein said catalyst bed is divided into two parts connected in series with about 50% of the mononitrobenzene compound and dinitrobenzene compound being fed to each of said two parts of catalyst bed.

18. The process of claim 16 wherein the mononitrobenzene compound is utilized as a diluent in said hydrogenation reaction.

19. The process of claim 13 wherein the temperature in the first of said two steps is at from about 40° to 70° C.

20. The process of claim 13 wherein the temperature in the second of said two steps is at from about 35° to 55° C.

21. The process of claim 19 wherein said first of said two steps is carried out in two stages in a main reactor and an auxiliary reactor, and the temperature in the main reactor is at from about 40° to 65° C. and the temperature in the auxiliary reactor is at from about 45° to 70° C.

22. The process of claim 12 wherein the temperature of the hydrogenation reaction is at from about 350° to about 650° F.

23. A continuous process for the co-production of mononitrobenzene and dinitrobenzene comprising the steps of reacting benzene with nitric acid and sulfuric acid in two steps, wherein in the first of said two steps a mixture of concentrated sulfuric and nitric acid is reacted with mononitrobenzene to provide a mixture of about 60% to about 80% mononitrobenzene and about 40% to about 20% dinitrobenzene and dilute sulfuric and nitric acids; separating said mononitrobenzene and dinitrobenzene from said acid mixture and then reacting in the second of said two steps said dilute nitric and sulfuric acid of said first of said two steps with benzene to provide mononitrobenzene, and using said mononitrobenzene in said first of said two steps.

24. The process of claim 23 wherein said nitration of benzene is controlled whereby said mixture of mononitrobenzene and dinitrobenzene is present at about 70% mononitrobenzene and about 30% dinitrobenzene.

25. The process of claims 23 or 24 wherein said mixture of mononitrobenzene and dinitrobenzene is separated from said dilute acid mixture by centrifugation or decantation.

26. The process of claim 23 wherein the temperature in the first of said two steps is at from about 40° to 70° C.

27. The process of claim 23 wherein the temperature in the second of said two steps is at from about 35° to 55° C.

28. The process of claim 26 wherein said first of said two steps is carried out in two stages in a main reactor and an auxiliary reactor, and the temperature in the main reactor is at from about 40° to 65° C. and the temperature in the auxiliary reactor is at from about 45° to 70° C.

29. A continuous process for the co-production of aniline and m-phenylenediamine from a mixture of from about 60% to about 80% mononitrobenzene and 40% to 20% dinitrobenzene comprising subjecting said mixture of mononitrobenzene and dinitrobenzene to a gas phase hydrogenation reaction comprising contacting said mixture in the gas phase with hydrogen in the presence of a catalyst to provide a mixture containing about 60% to about 80% aniline and about 40% to about 20% m-phenylenediamine, and separating said aniline and m-phenylenediamine from said mixture.

30. The process of claim 29 wherein said hydrogenation is carried out by passing said mixture of mononitrobenzene and dinitrobenzene when in the gaseous form in the presence of hydrogen gas through a catalyst bed.

31. The process of claim 30 wherein said catalyst bed is divided into two parts connected in series with about 50% of the mononitrobenzene and dinitrobenzene being fed to each of said two parts of catalyst bed.

32. The process of claim 29 wherein aniline is utilized as a diluent in said hydrogenation product.

33. The process of claim 29 wherein the temperature of the hydrogenation reaction is at from about 350° to about 650° F.

* * * * *